US010300182B1

(12) United States Patent
Brar

(10) Patent No.: US 10,300,182 B1
(45) Date of Patent: May 28, 2019

(54) ANTIMICROBIAL DEVICE FOR WOUND CARE

(71) Applicant: Harjeet S Brar, Bakersfield, CA (US)

(72) Inventor: Harjeet S Brar, Bakersfield, CA (US)

( * ) Notice: Subject to any disclaimer, the term of this patent is extended or adjusted under 35 U.S.C. 154(b) by 0 days.

(21) Appl. No.: 15/458,382

(22) Filed: Mar. 14, 2017

Related U.S. Application Data

(63) Continuation-in-part of application No. 14/717,936, filed on May 20, 2015.

(51) Int. Cl.
*A61M 1/00* (2006.01)
*A61N 5/06* (2006.01)
*A61M 35/00* (2006.01)
*A61M 37/00* (2006.01)

(52) U.S. Cl.
CPC ........ *A61M 1/0088* (2013.01); *A61M 1/0058* (2013.01); *A61M 35/00* (2013.01); *A61M 37/0092* (2013.01); *A61N 5/0616* (2013.01); *A61M 2205/3331* (2013.01); *A61M 2205/3368* (2013.01); *A61M 2205/3584* (2013.01); *A61M 2205/505* (2013.01); *A61N 2005/0661* (2013.01)

(58) Field of Classification Search
CPC ............ A61M 1/0088; A61M 37/0092; A61M 1/0058; A61M 35/00; A61M 2205/3584; A61M 2205/3331; A61M 2205/3368; A61M 2205/505; A61N 5/0616; A61N 2005/0661
See application file for complete search history.

(56) References Cited

U.S. PATENT DOCUMENTS

| | | | |
|---|---|---|---|
| 4,475,900 A | 10/1984 | Popovich et al. | |
| 5,334,166 A | 8/1994 | Palestrant | |
| 5,620,424 A | 4/1997 | Abramson | |
| 5,695,482 A | 12/1997 | Kaldany | |
| 6,461,569 B1 | 10/2002 | Boudreaux | |
| 7,947,021 B2 | 5/2011 | Bourne et al. | |
| 2007/0141128 A1* | 6/2007 | Blott | A61M 1/0058 424/445 |
| 2008/0051736 A1 | 2/2008 | Rioux et al. | |
| 2010/0106103 A1 | 4/2010 | Ziebol et al. | |
| 2011/0213339 A1 | 9/2011 | Bak | |
| 2011/0276115 A1* | 11/2011 | Merrill | A61F 7/12 607/106 |

(Continued)

OTHER PUBLICATIONS

Haaland, Carter, "Fellows invent UV catheter sleeve," mndaily.com, Sep. 22, 2009 (US).

(Continued)

*Primary Examiner* — Lauren P Farrar
(74) *Attorney, Agent, or Firm* — R. Scott Kimsey, Esq.; Klein DeNatale Goldner

(57) ABSTRACT

A wound care device includes a flexible cover having a concave interior surface and a flange configured for sealing engagement with the skin of a patient so that the device can be affixed to the skin of the patient. An inlet tube is in fluid communication with the interior thereof and configured to deliver a fluid compound thereto. An outlet tube extends from the flexible cover and is in fluid communication with the interior thereof to allow aspiration of fluid from within the flexible cover. A programmable system delivers one or more of oxygen, saline, medicaments, UV light, and ultrasonic vibration on a schedule predetermined by a user of the device.

11 Claims, 8 Drawing Sheets

(56) References Cited

U.S. PATENT DOCUMENTS

| | | | |
|---|---|---|---|
| 2013/0165821 A1* | 6/2013 | Freedman | A61F 13/00063 |
| | | | 601/2 |
| 2014/0052054 A1* | 2/2014 | Quisenberry | A61F 7/02 |
| | | | 604/23 |
| 2014/0207027 A1* | 7/2014 | Navia | A61F 13/00068 |
| | | | 601/6 |

OTHER PUBLICATIONS

Author Unknown, "Medical device infection control system for sterilization of catheter access point with ultraviolet light," Regents of the Univ. of Minnesota, Jun. 25, 2010, US.

Author Unknown, "Ultra-Clean Catheter Site Disinfection System," UVSolution, Nov. 3, 2011 (US).

\* cited by examiner

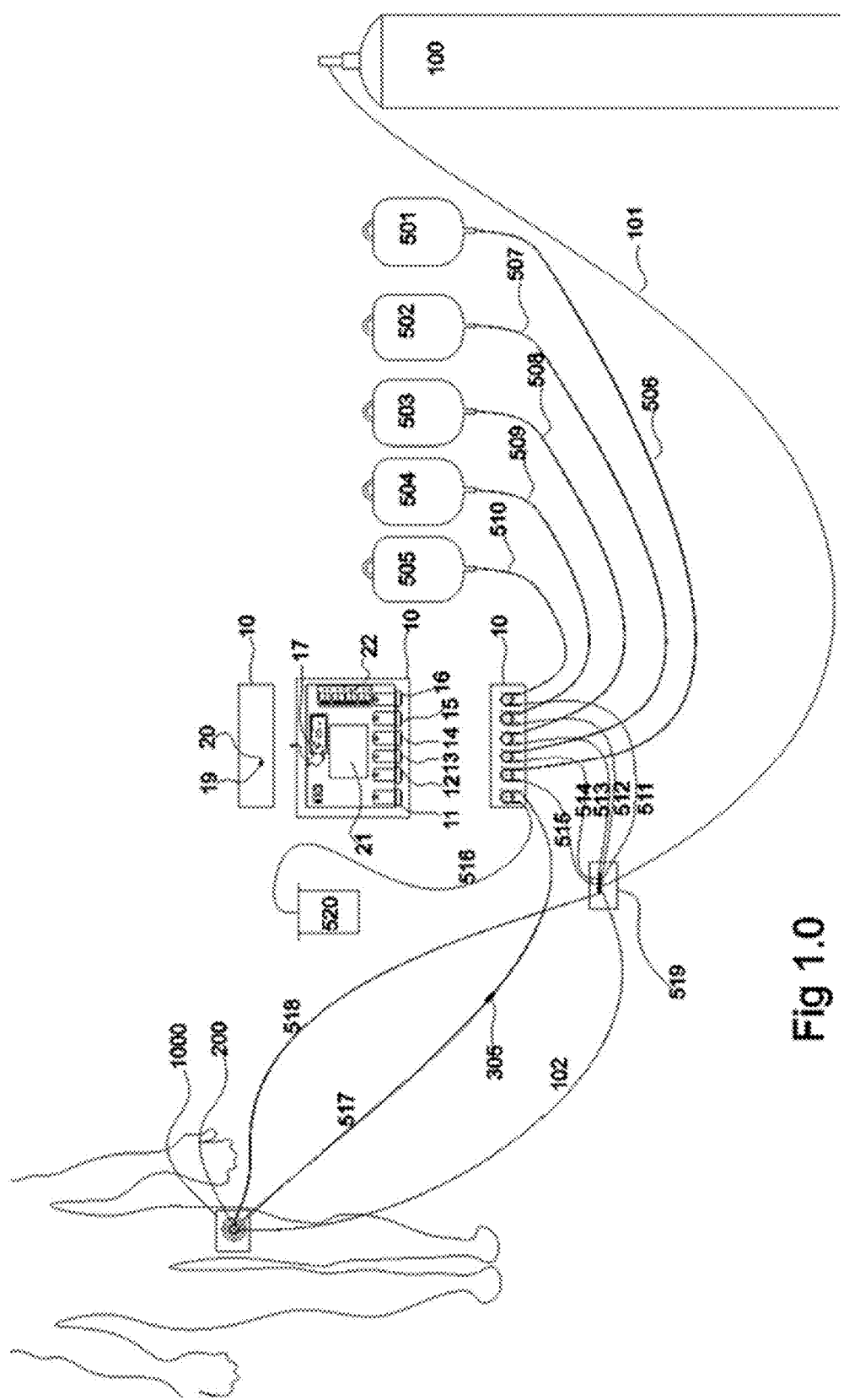
Fig 1.0

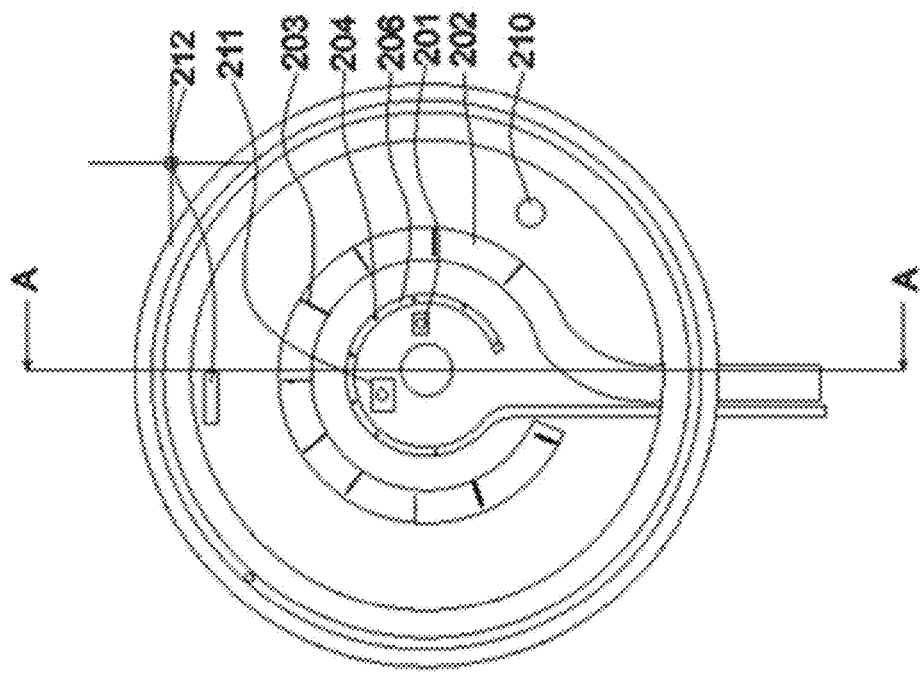
Fig 2.1
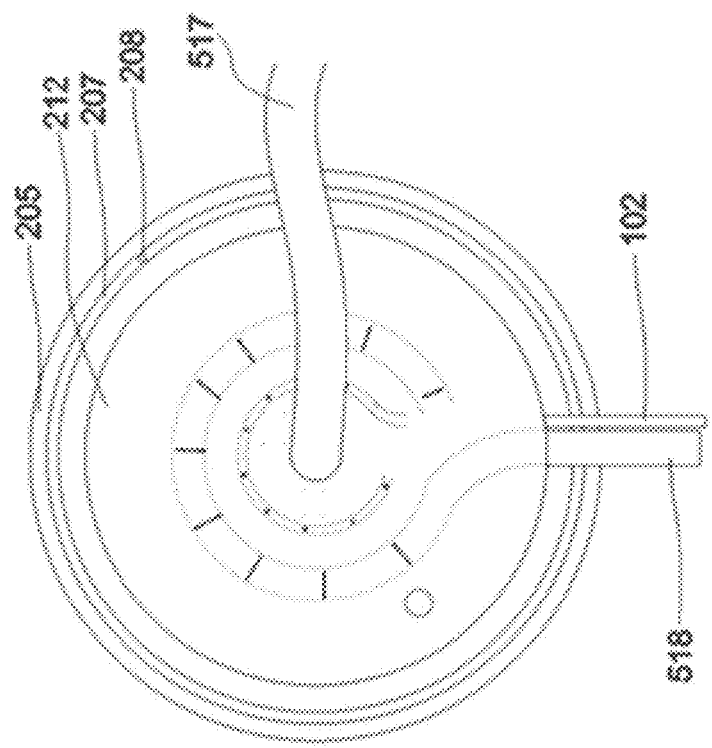
Fig 2.0

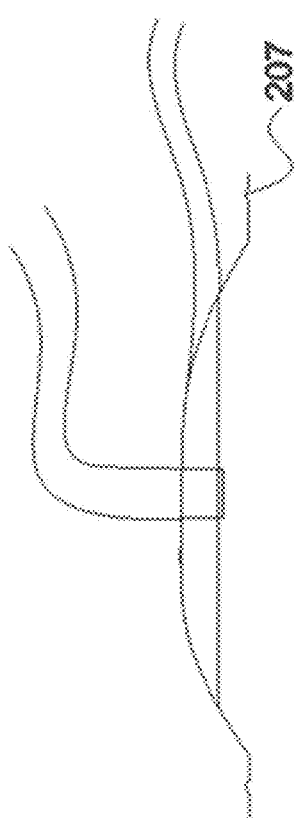
Fig 2.2
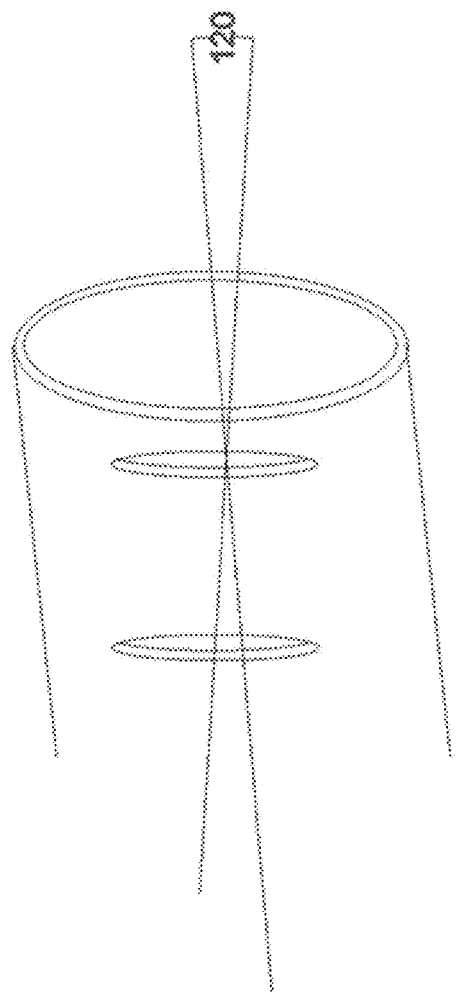
Fig 2.3

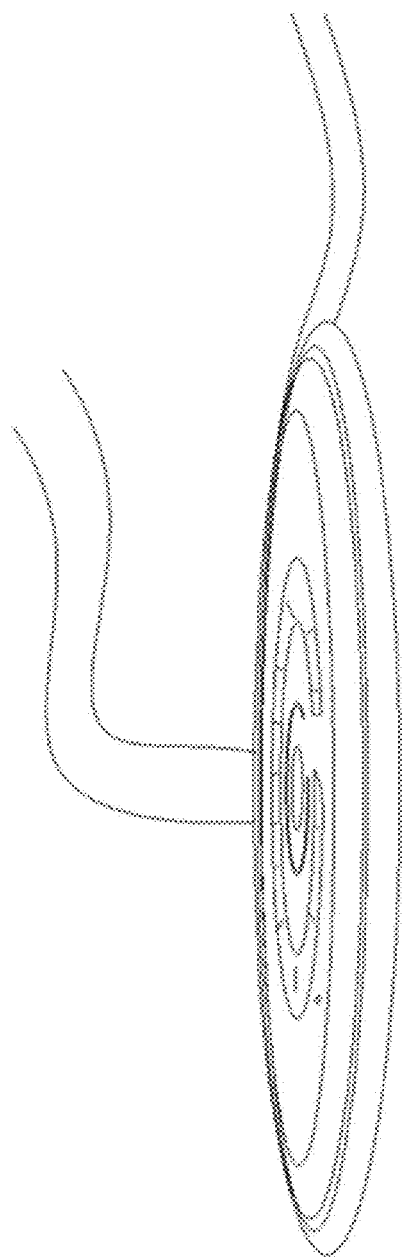
Fig. 2.4

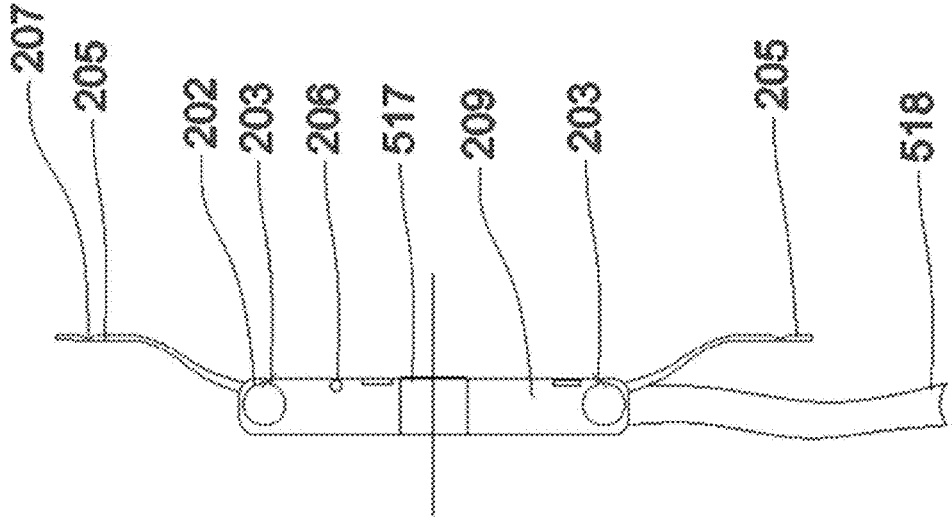

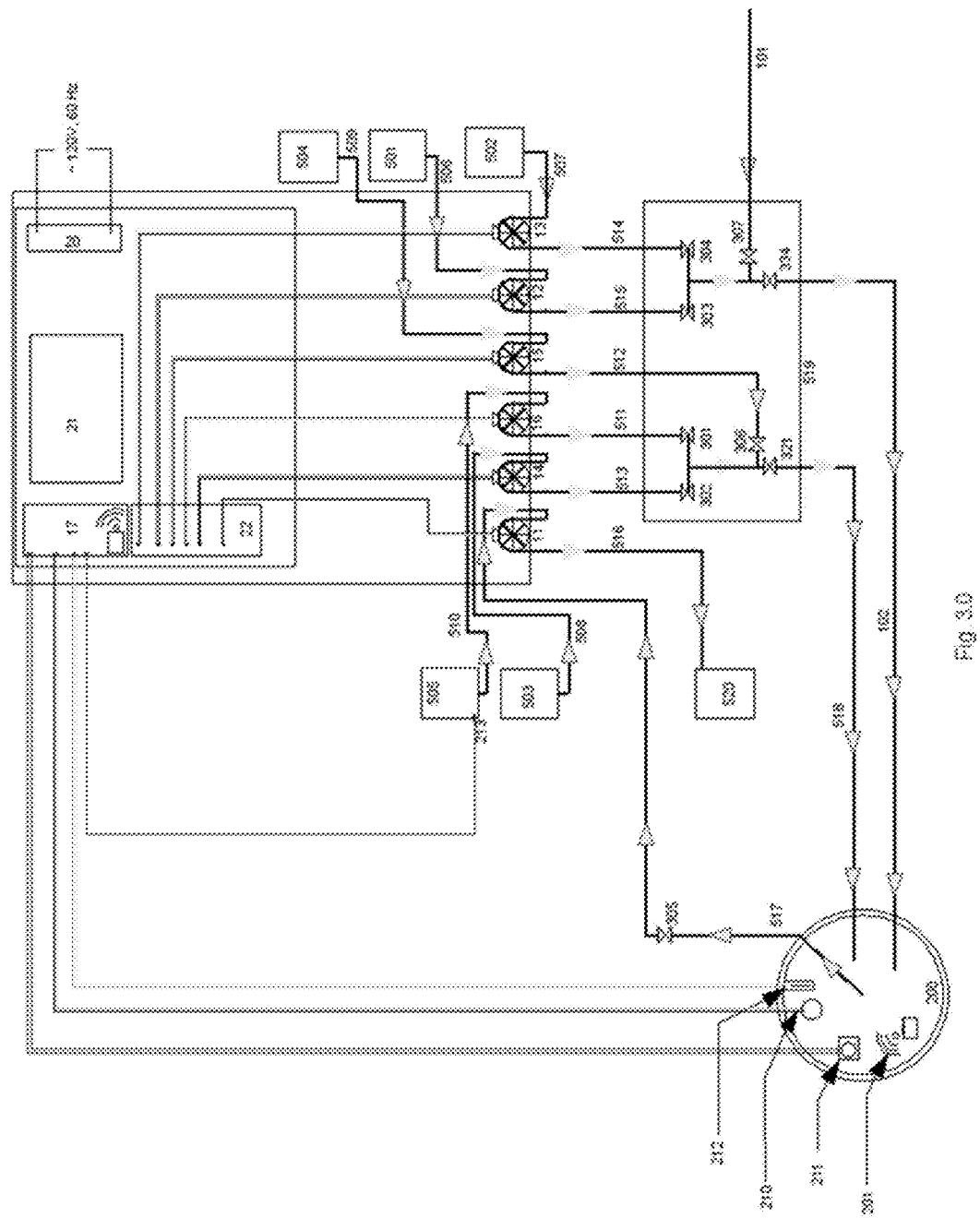

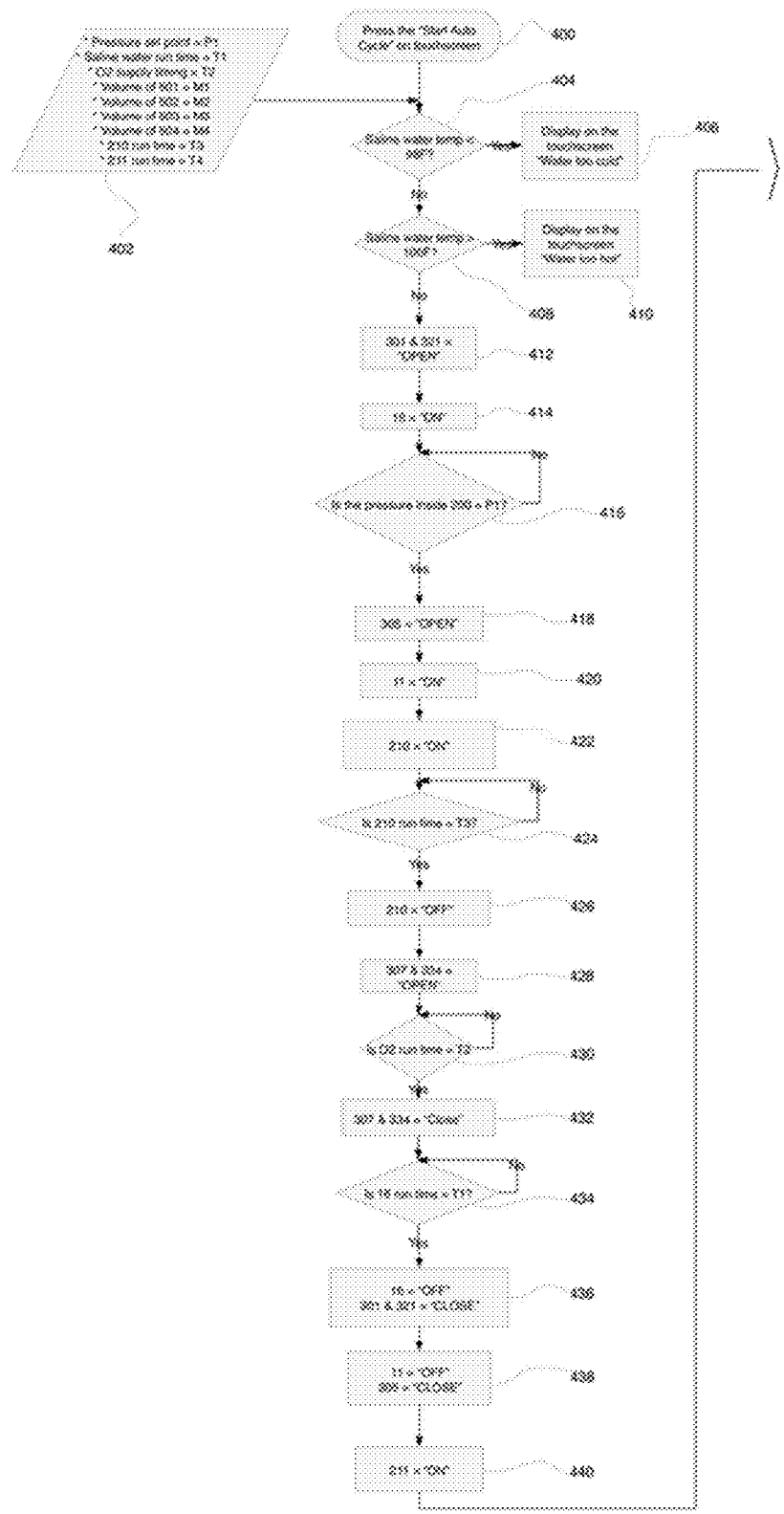
FIG. 4.1

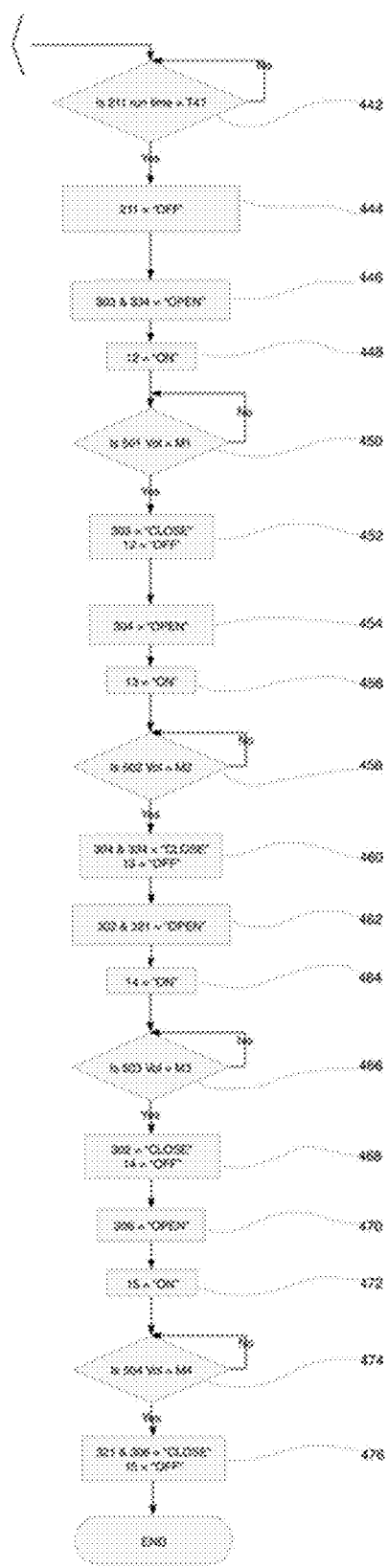
FIG. 4.2

ANTIMICROBIAL DEVICE FOR WOUND CARE

RELATED APPLICATIONS

This application claims priority of U.S. patent application Ser. No. 14/717,936, filed May 20, 2015 and entitled "Antimicrobial Wound Care Device," which application is incorporated herein by reference.

BACKGROUND OF THE INVENTION

1. Field of the Invention

The present invention relates generally to the field of wound care, and more specifically to a portable, automated device for eliminating or reducing the presence of viable microorganisms at the site of a wound or on the surface of an instrument inserted through a wound. The invention also relates to improving healing of tissues at or near a wound site through automated cycles of increased oxygenation, cleaning and medication of the tissues at the local area, and changing the gaseous concentration around the wound area such that it is not conducive to the growth of a pathogenic organism. The invention also relates to using ultrasound waves and ultraviolet light to promote healing of tissue at or near the wound site. Oxygen levels in the local area may be increased without the need for expensive hyperbaric chambers.

2. Background

Infection at the site of a wound is always a serious concern for health care providers, whether due to microorganisms exposed to the patient outside of the healthcare facility or within the healthcare facility, where microorganisms are prevalent. The 'wound' may be the result of accident or other trauma, or may be intentional, such as the wound that results from the insertion of a hemodialysis catheter or other instrument into the patient's body. Any puncturing of the epidermis produces a wound that may be susceptible to infection.

A portable automated device for reducing the risk of infection at the site of a wound is needed.

SUMMARY OF THE INVENTION

The present invention provides a device for protecting against microbial infection. The device includes a cover having a concave interior surface and a convex exterior surface. The device further includes an adhesive flange for affixing the cover to a patient's skin. The center piece of the cover may be thicker as compared to the cover, to embed the inlet and outlet tubes. The center piece and the cover may be of the same flexible material and may be defined as one structure.

In another aspect of the invention, the device includes inlets extending through the center piece of the cover. The inlets define the opening for introducing saline water, anti-microbial compound and oxygen into the space between cover and wound.

In another aspect of the invention the inlets are the polymer tubes extending through the cover and are embedded in the center piece in circular orientation. The inlets are embedded concentric to the center piece in opposite orientation to each other i.e. clockwise and anticlockwise.

In another aspect of the invention, the inlet tubes are angular holes throughout the circular orientation that extend inside the device cover, to introduce anti-microbial compound, saline water or gas in the space between wound and cover. One of the inlet tubes preferably includes an axis of holes at an angle to the central axis of the inlet tube to promote a whirlpool phenomenon of the saline water by introducing it at an angle between the cover and wound.

In another aspect of the invention, the device includes a drainage structure, an outlet, that extends through the center of the center piece of the cover. The outlet moves the fluids, gas and any other non-value added material from the space between the cover and the patient's skin into the drainage structure for disposal.

In another aspect of the invention, the antimicrobial compound, saline water and oxygen are delivered to the device using a programmable control device (PCD). Programmable control device (PCD) includes pumps, touchscreen, electronic board and a software program to operate the device.

Another aspect of the invention provides a device for protecting against antimicrobial infection that includes a port opening, that extends through the cover, to enable the remote monitoring of the wound via a camera.

In another aspect of the invention, the oxygen level inside the device cover is monitored using an oxygen sensor.

Another aspect of the invention includes a trough in the surface of the flanged edge that comes in contact with patient skin. The trough consists of an opening that extends through the cover. This opening is used to create a negative pressure in the trough to secure the device to the skin. Another mechanical method may also be used to secure the device to patient's skin.

In another aspect of the invention, the cleaning of wound is achieved by creating a liquid media based whirlpool cleaning mechanism to remove the dead tissue and other anti-wound healing micro-organisms at pre-programmed frequency and duration using the programmable control device (PCD). The liquid whirlpool between the device and the wound are created by the combination of controlled pressure and directional flow of saline water using an angular orientation of holes in the inlet tubes. Oxygen may be used to enhance the effectiveness of whirlpool through the other inlet tube.

In another aspect of the invention, the programmable control device (PCD) is used to provide controlled temperature and humidity to the wound on programmed duration and frequency.

In another aspect of the invention, the fluids, gas and antimicrobial gels may be pre-heated to the desired temperature, before introducing between the cover and the wound, with the help of programmable control device (PCD), to promote the healing process of wound.

Another aspect of the invention relates to the customization of the shape of the device around the wound by scanning the site of the wound with a 3D scanner. The flange/device may then be customized to precisely fit around the site so there is minimal or no leakage of the contents. The flange can be made of flexible polymer/silicone and 3D printer may be used to custom print the device directly at the point of use. Open source 3D programming may be used to scan the wound site as well as to customize the creation of the device. Use of such a custom version of the device may add comfort and utility to the device.

The antimicrobial compound used with the present device may be a gas, a liquid, a gel, an oxidizing agent, or any other suitable agent.

In another aspect of invention, the programmable control device is connected to the inlet and outlet tubes of the device. The programmable control system will utilize a programming language to program the sequence of treatment throughout the lifecycle of wound.

In another aspect of the present invention the embodiment of the present device is airtight when affixed to a patient's skin via the adhesive flange and negative pressure established in the trough so as to maintain a constant state within the interior of the device over a desired treatment period.

The constant state within the interior of the device may include any gas or combinations of gases, or may include a vacuum.

The programmable control device may include a LCD/TFT touchscreen for operator interface, multi-pumping system, temperature and pressure sensor, heating element, Wifi, LAN and Bluetooth™ connection capabilities and internal and external power source. Programmable control device may include remote operation capabilities through IR remote.

One embodiment of a device of the present disclosure includes a flexible cover having a concave interior surface and a flange configured for sealing engagement with the skin of a patient so that the device can be affixed to the skin of the patient. A inlet tube is provided in fluid communication with the interior thereof and configured to deliver a fluid compound thereto. An outlet tube extends from the flexible cover and is in fluid communication with the interior thereof to allow aspiration of fluid from within the flexible cover.

The inlet tube may be embedded in the flexible cover in a concentric configuration. The outlet tube may define a drainage path from the interior of the flexible cover to the exterior of the flexible cover.

The inlet tube may define a plurality of openings along the length thereof and within the interior of the flexible cover.

The openings defined in the inlet tube may be defined at an angle greater than ninety degrees to the longitudinal axis of the tube.

In some embodiments of a device of the present disclosure, the inlet tube may be a first inlet tube, and a second inlet tube may be embedded in the flexible cover in a concentric configuration opposing that of the first inlet tube. The second inlet tube is in fluid communication with the interior of the flexible cover.

The device may further include a sensor embedded in the interior surface of the flexible cover.

The flange of the flexible cover may include a trough extending along a perimeter thereof. An opening may be defined in the wall of the trough and in fluid communication with the interior thereof, for creating negative pressure within the trough.

The device may further include an ultrasonic transducer embedded in the flexible cover.

The device may further include a port defined by the flexible cover and configured to receive a camera. A camera may be affixed to the port and positioned to provide an interior view of the flexible cover.

Another embodiment of the present disclosure may provide a system for treating the wound of a patient. The system may include a flexible cover having a concave interior surface and a flange configured for sealing engagement with the skin of a patient, for affixing the cover to the skin of the patient. An inlet tube may be embedded in the flexible cover and in fluid communication with the interior thereof, and configured to deliver a fluid compound to the interior of the flexible cover. An outlet tube may extend from the flexible cover and be in fluid communication with the interior thereof to allow aspiration of a fluid from the interior of the flexible cover. An ultrasonic transducer and ultraviolet light source may be provided embedded in the flexible cover. A saline reservoir, oxygen reservoir, and medicament reservoir may be included as part of the system, each in fluid communication with the inlet tube. A programmable control system may be in electronic communication with the ultrasonic transducer, the ultra-violet light source, at least one inlet pump configured to deliver the saline solution, oxygen, and/or medicament to the interior of the flexible cover, and an outlet pump configured to drain fluid from the interior of the flexible cover via the outlet tube. The programmable control system may be programmed by the user of the system to alternately provide ultrasonic vibration, ultraviolet light, saline, oxygen, or a medicament to the wound area within the flexible cover, according to a schedule determined by the user.

BRIEF DESCRIPTION OF THE DRAWINGS

FIG. 1.0 is a general schematic view one embodiment of a programmable control device of the present disclosure, along with various connections to other components of the present system.

FIG. 2.0 is a top view of one embodiment of an antimicrobial wound care device of the present disclosure.

FIG. 2.1 is a bottom view of one embodiment of an antimicrobial wound care device of the present disclosure.

FIG. 2.2 is a side view of one embodiment of an antimicrobial wound care device of the present disclosure.

FIG. 2.3 is the detailed view of one embodiment of an inlet tube with an angular orientation of holes therein.

FIG. 2.4 is the bottom angular view of one embodiment of an antimicrobial wound care device of the present disclosure.

FIG. 2.5 is a further detailed view of the section A-A from FIG. 2.1.

FIG. 3.0 is a schematic diagram of various components of the present system.

FIG. 4.1 is a first portion of a flowchart showing the program operation of the auto cycle function of the present system.

FIG. 4.2 is a second portion of the flowchart of FIG. 4.1

DETAILED DESCRIPTION OF THE INVENTION

Certain terms used herein refer to the orientation of the present device, or to the top or bottom thereof. As used herein, the word top, and like words, refers to the exterior, convex surface of the cover of the present device. This holds true whether the device is oriented so that this surface extends upward, such as when the device is positioned atop a wound on a patient's skin, or when the device is positioned on the underside of a patient's skin. Likewise, the interior, concave surface of the cover of the present device may be referred to as the bottom of the device, regardless of the actual orientation of the device. Use of the words top and bottom, or any such directional terms, for other parts of the present device are to be interpreted in a manner consistent with the 'top' and 'bottom' of the cover, as defined above.

The term 'wound' is also used herein, and refers to any break in the integrity of the epidermis of a patient, whether that break is accidental, or is the result of an intentional break in the epidermis, such as for the insertion of a catheter or other instrument.

The term antimicrobial compound is used broadly herein to refer to any compound that achieves an antimicrobial effect in situ. Thus, the term may refer to compounds, such as antibiotics, that are directly antimicrobial in function, or to compounds such as hydrogen peroxide, which achieve an antimicrobial effect only by reaction with another compound (in the case of hydrogen peroxide, the enzyme catalase). Further, as defined herein, $O_2$ is considered an antimicrobial compound for purposes of the present invention, when present at sufficient concentration to have an antimicrobial effect. The form of the antimicrobial compound may include a liquid, gas, gel, or any other suitable form of compound.

Turning now to the drawings, wherein like numerals indicate like parts, FIG. 2.0 is a top view of one embodiment of an antimicrobial device 200 of the present invention. FIG. 2.1 shows the bottom view of a preferred embodiment of the wound care device. The wound care device 200 preferably includes circular tubes 202 and 206 embedded in the center piece of the device. Tube 202, as shown in FIG. 2.1, has angled holes 203 coming through the center piece and body of the device 200 to introduce fluid in an angular direction between device 200 and wound. FIG. 2.3 illustrates the details of the angled orientation of holes 203 to the axis of tube 202. Tube 202 is connected to tube 518 and further to the manifold 519 as shown in FIG. 1.0. As shown in FIG. 2.1, tube 206 includes, through the body of the device 200, holes 204 to spray and distribute fluid and oxygen supplied from the manifold 519 using tube 102 as shown in FIG. 1.0. FIG. 2.2 shows the side view of a preferred embodiment of the wound care device. As shown in FIG. 2.0, device 200 includes a drain tube 517 connected at the top of the device 200. FIG. 2.5 shows the cross section detail A-A of the FIG. 2.1. FIG. 2.5 shows the orientation of tubes inside the center piece 209.

In a preferred embodiment shown in FIG. 1.0, the programmable control system 10 is used to supply the saline water, medication and controlled environment to the wound care device 200 shown in FIG. 2.0 (top view) through different combination of programmable and manual settings, to promote the wound healing process. Control system 10 preferably includes saline pump 16, medicine pumps 12, 13, 14 and 15, drain pump 11, operator interface touchscreen TFT 21, and relay module 22 and control circuit board 17. The control circuit board 17 preferably includes Wi-Fi and Bluetooth™ capabilities to connect to a network and other wireless capable devices for communication. A Wi-Fi camera system 201 may be installed on the wound care device 200 for remote monitoring the wound. Circuit board preferably includes a USB connection 19. The control system 10 preferably includes an internal and an external power source 20. Wound care device 200 may be connected from its edge 205 (FIG. 2.0) to the skin of a patient using a water tight clear adhesive sheet 1000 (FIG. 1.0). Wound care device 200 may also be sealed to skin by creating negative pressure in the trough 207 using hole 208. Wound care device 200 is connected to the manifold 519 using tubes 102 and 518. FIG. 3.0 shows the details of the manifold 519. Manifold 519 consists of 8 activated vales 301, 302, 303, 304, 306, 307, 321 and 334. Wound care device 200 may also be connected to the inlet of drain pump 11 using tube 517. Valve manifold 519 is connected to outlets of pumps 12, 13, 14, 15 and 16 using tubing 515, 514, 513, 512 and 511 respectively. Inlet of pumps 12, 13, 14, 15 and 16 are connected to the fluid medical or other supplies 501, 502, 503, 504 and 505 respectively using tubes 506, 507, 508, 509 and 510 respectively. Manifold 519 is connected to oxygen supply 100 via tube 101. Outlet of the drain pump 11 is connected to drain collection system 520 via tube 516 and valve 305 as shown in FIG. 3.0. In programmable mode following cycles may be executed in the below order:

Cleaning cycle
Medication cycle
Controlled environment cycle

In auto cycle mode (selected by the operator using the TFT operator interface 21) during the cleaning cycle, first, saline water pump 16 turns ON, draws pre-heated saline water from supply 505 using tubing 510, and delivers it to manifold 519 via tubing 511. Saline water is delivered to the wound care device 200 using the tube 518 at programmed rate. Pre-heated saline water is distributed to the wound using tube 202 through holes 203 to create a whirlpool of the saline water with a combination of angular water jets and oxygen supply through holes 204 of tube 206. Timing of saline water and oxygen supply are controlled by different programmable variables.

Once the whirlpool of heated saline water is sustained and the wound care device is filled with saline water, the drain pump is turned "ON" based on the programmable control of variables like pressure, time and flow. Drain pump 11 drains the mixture of saline water, oxygen and debrided wound tissue from the wound care device 200 using tube 517 and further drains into a drain collection system 520 using tube 516. Saline water, air and drainage continues until the desired state of wound is achieved based on the programmable variable; time.

Ultrasonic wave generator (piezoelectric crystal/transducer) 210, as shown in FIG. 2.1, may be activated for a programmable time to promote wound healing. This is preferably done while the space between wound care device and wound is filled with saline water.

Once the desired state of wound is achieved, the programmable control system turns off the saline water pump 16 and oxygen supply from 100. Drain pump 11 is turned off after a time lag programmed based on the wound characteristics.

Ultraviolet light source, 211, as shown in FIG. 2.1, may be turned on for a pre-programmable time to expose the wound area to ultraviolet light to enhance the healing. This step is preferably performed before applying the medication to wound and after the cleaning cycle.

In the medication cycle, pumps 12, 13, 14 and 15, individually or in combination, deliver medication respectively from medical supplies 501, 502, 503 and 504 to the pump inlets via tubing 506, 507, 508 and 509. The dosage of each medication is controlled using programmable variables and wound characteristics. Depending on the medication type, tubing 518 and 102 are used to deliver medication to the wound care device 200 from manifold 519. Inside the wound care device 200, the medication is evenly distributed to the wound through holes 203 or 204, depending on the source of medication. In the controlled environment cycle, the controlled environment is maintained inside the wound care device 200 by supplying oxygen from the source 100, first to the manifold 519 using tube 101 and from manifold 519 to wound care device 200 via tube 102.

In the auto cycle mode, all the above-mentioned cycles will be repeated at a pre-programmable frequency based on the wound characteristics.

The operator interface TFT 21 preferably includes options for the operator to manually select the cleaning cycle, medication cycle or controlled environment cycle to start anytime, independent of the auto cycle option. In each of the various embodiments of the present invention, the device serves to maintain a steady state of antimicrobial activity.

This is in marked contrast to the use, for example, of antimicrobial ointments in combination with bandages and the like. In such circumstances, an initial high level of antimicrobial activity is provided, however that initial peak of antimicrobial activity drops substantially over a relatively short period of time. The present device creates a steady state of antimicrobial activity so that there is no "peak" followed by an undesirable drop-off in antimicrobial activity. This not only decreases or inhibits antimicrobial growth, but also facilitates healing at the site of the wound and reduces the risk of antimicrobial resistance emerging among the population of pathogenic microorganisms at the wound site.

In some embodiments of the invention, various components of the invention may be constructed of a flexible or malleable material that may be shaped by the end user to a desired conformation. This is particularly useful in terms of shaping one or more of the conduits of the present invention to fully surround a wound, or to conform as best as possible to the shape thereof, or in shaping the device as a whole, such that the flange takes on a customized conformation for attachment to the skin of the patient. Such shaping may take into account the area on the patient's body where the device is to be placed, the contours of the patient's skin, and so on.

In other embodiments of the invention, the present device may be custom-made at the point of use such that it has the necessary or desired dimensions for a given wound treatment. A digital camera, scanner, or other such device may be utilized to scan or photograph the area of the wound desired to be treated. Once the necessary data is acquired, a 3D printer may be used to "print" various components of the device, such as, for example, the flange, cover, and the like so that it conforms to the shape and size of the wound being treated. In some embodiments, wherein the various membranes or conduits described above are replaced with structures having physical openings capable of being reproduced with a 3D printer, the entire device may be printed in such a manner.

Further Principles and Alternatives

It is to be understood that the invention disclosed herein is suitable for use in a variety of manners, incorporating various principles of wound management. For example, when wound care calls for the use of antibiotic treatments, the present device may be utilized to maintain deliver of antibiotics to the wound site.

Further, the present device may assist in wound debridement, which is vital to treatment of wounds having contamination or other material therein. The inlet ports of the various embodiments of the invention may be used to introduce fluids for use in debridement, the fluids and accompanying contaminants being aspirated from the wounds via the ports provided for that purpose.

Likewise, irrigation of a wound may be provided using the present device. For example, a warm, isotonic saline solution may be introduced to the wound site using the present device, and irrigation fluid may matter loosened from the wound site may be aspirated in the manner described above.

In some wound care applications, enzymatic debridement is used, wherein exogenous enzyme is applied to the wound site for debridement or other functionality. It is contemplated that the introduction of exogenous enzyme solutions to a wound site may be accomplished via the present invention, and the aspiration of such material, when necessary, may also be accomplished as described above.

Other topical treatments may also be applied to, and maintained at, a wound site using the present device. These include growth factors important in wound healing, antiseptic agents, foam dressings, and the like.

The various components of the embodiments described above and shown in the drawings may be connected in any suitable manner. Some components, such as tubes, are in fluid communication, and may be provided as single, contiguous portions of material or may be multiple portions of material attached by adhesives, heat, or other known processed. Components not in fluid communication may likewise be manufactured as single pieces, attached by adhesives, heat processes, and so on. It is contemplated that various methods or processes for attaching the components of the present device are well known in the art.

The foregoing descriptive and accompanying illustrations are intended to be exemplary of the principles of the present invention. Various modifications to the description provided herein will be readily apparent to one of ordinary skill in the art upon reading this disclosure, and it is contemplated that such modifications are within the spirit and scope of the present invention.

Individual Components and Operation Description:

Individual components and precise operation of the components of a preferred embodiment of the invention are described in more detail in sections which follow:

Temperature Sensor

As shown in FIG. 3.0; a temperature sensor 213 is used to sense the temperature of the saline water. This temperature is used as an input to turn on the saline water pump. The performance requirements for commercial embodiments of temperature sensors are that they should be accurate to ±0.1° F. and stable to ±0.02° F. The sensor should have a response time of 0.1 seconds, and dimensions no larger than 0.5 mm in diameter and 1 mm in length. Accuracy requirements are subject to medical review. Most sensor technologies can meet these requirements on a prototype basis but thermocouple technology will be best suited for mass production to achieve the required degree of reproducibility to make it a cost-effective solution.

Pressure Sensor

A pressure sensor 212 will be embedded in the body of the flexible wound care device to sense the pressure between the wound care device and wound. Pressure sensor output will be used as the input for drain pump (11) and valve (305) as shown in FIG. 3.0. Pressure sensor should be a flexible type and should be able to stick. The force sensitive range for the sensor should be 100g to 10 kg. Sensor length should be less than 2.5" and width should be less than 1". Pressure sensor FSR402 is a viable option to use in the prototype.

Valve Manifold

As shown in FIG. 3.0, a valve manifold 519 is used to control the flow of saline water, oxygen, drain and medication. The manifold will have at least six inlets and two outlets. Manifold will consist of at least eight check valves to control the flow of liquids and gas. These are off the shelf 2.5 to 4 mm manifold and valves that are suitable for the prototype application. The maximum flow required through the manifold is not to exceed 60 ml/min @ 3-4 psig. Combinations of different check valves are also suitable for the application if a manifold is not a cost-effective solution.

Microcontroller Board

As shown in FIG. 3.0, programmable control circuit board, 17 and a relay module, 22 is used to control the pumps and sensors by using digital and analog inputs and outputs. For the prototype purpose an open source microcontroller board with digital and analog inputs and outputs is sufficient. A board with 54 pin output/input (Combination of PWM, analog, digital), four UARTs, USB connection, WiFi module, Ethernet connection and Bluetooth™ 3.0 connection is sufficient for prototype. The microcontroller board will run on DC power with 5V operating voltage. The recommended input voltage for microcontroller board will range from 7-12V. Board should have at least 256 KB of flash memory to store the programs.

Pumps

As shown in FIG. 3.0, six pumps are used in the wound care device to deliver saline water and medications to the wound and drain the residual from the wound. All six pumps can be of the same specification. A micro peristaltic liquid pump with silicon tubing can is sufficient for prototype. The silicone tube diameter can range from 1/8" to 3/16" OD. The pumps with working temperature range of 0° C. to 100° C., motor voltage 12 VDC, motor current 200-400 mA, Flow rate of up to 100 mL/min and total length of 50-65 mm with a diameter that should not exceed 30 mm is suitable for prototype application. These pumps should be compatible to PWM output of the microcontroller board to control the flow of the liquid through the pump. A separate 12 VDC power source, from microcontroller, may provide the power to pumps.

Ultrasonic Transducer

As shown in FIG. 3.0, an ultrasonic transducer 210 is embedded in the wound care device to create the ultrasonic waves in the saline water to promote wound healing process. A piezoelectric ultrasonic ceramic transducer is sufficient for prototype application. A 30-40 W piezoelectric ceramic with frequency range of 30-40+/−1 kHz, a max OD of 50 mm, thickness range of 2-3 mm, with low heat and good thermal stability is sufficient. A separate generator with 12-15 VDC power, and frequency generation range of 8 KHz-40 kHz may be used to activate the piezoelectric ceramic. This generator is controlled using the microcontroller circuit board.

Ultraviolet Light Source

As shown in FIG. 3.0, an ultraviolet light source 211 is embedded in the wound care device to help disinfection in the wound. An ultraviolet light source with 265 nm-280 nm (+/−5 nm) wavelength is appropriate. The light source is recommended to base on the LED technology to reduce the size of the source. A UV LED light source with a max. forward voltage of 7 v, max forward current of 30 mA, peak wavelength of 265 nm-280 nm, viewing angle of at least 120 degrees, max. operating temp of 20° C. is suitable for prototype application. 3.5×3.2×1.1 mm (W×L×H) is suitable for this application.

WiFi Camera

As shown in FIG. 3.0, a Wifi enabled micro camera 201 will be installed in the wound care device. A Wifi enabled, with a range of 0-20 m distance in P2P mode and no restricted distance in network IP mode, built in rechargeable battery, preferably a minimum of 640*480 resolution, view angle of 40-60 degrees and power requirement of 5V, 1 A is suitable for this application. A camera with a maximum size of 7 mm×7 mm is preferred for prototype application.

Operation of Wound Care Device

Auto-cycle operation of wound care device is explained using the process flow diagram showed in FIGS. 4.1 and 4.2.

Once the wound care device 200 is affixed to the patient's skin, the programmable control device 10 is turned on by pressing "Start Auto Cycle" button on the touchscreen 21 of the programmable control system (Step 400). Next, the user interface touchscreen 21 prompts the user to input continuous variable value (Step 402) for the following variables, one at a time:

Pressure set point to turn drain pump and drain valve "ON", P1;
Saline water run time, T1;
Oxygen supply time, T2;
Volume of medication 501, M1;
Volume of medication 502, M2;
Volume of medication 503, M3;
Volume of medication 504, M4;
Run time of ultrasonic transducer, T3; and
UV light run time, T4.

After the user enters all the variables; device checks the temperature of the saline water using sensor 213 (Step 404 and 408). If saline water temperature is less than 98° F., touchscreen displays "Water too cold" and halts the operation (Step 406). If saline water temperature is greater than 100° F., touchscreen displays "Water too hot" and halts the operation (Step 410). Program does not go to the next step until the saline water temperature is between 98° F. and 100° F. or user overrides the screen.

If the saline water temperature is between 98° F. and 100° F., the position of valve 301 and 321 is changed from closed to open (Step 412) and pump 16 is turned on (Step 414) to supply saline water to the wound care device (200). Saline water supply will continue till the pressure inside the wound care device is less than the input pressure value P1 (Step 416).

Once the pressure between the device 200 and wound is equal to the input pressure value P1; the position of drain valve 305 is changed from "CLOSE" to "OPEN" (Step 418) and pump 11 is turned "ON" (Step 420) to drain the saline water and debris to the drain collection system. At the same time, ultrasonic transducer 210 is also turned "ON" (Step 422).

Next, the software program checks if the run time for the ultrasonic transducer is equal to the input time, T3 (Step 424). Once the run time equals input time, T3, ultrasonic transducer is turned "OFF" (Step 426) and valves 307 and 334 are changed from "CLOSE" position to "OPEN" (Step 428) to initiate the supply of oxygen.

Once the oxygen supply run time is equal to the input time value T2 (Step 430), valves 307 and 334 are changed from "OPEN" position to "CLOSE" (Step 432).

Software program then checks if the run time for saline water is equal to the input time T1 (Step 434). If the run time is less than T1 then the saline water pump (16) continues to run otherwise saline water pump (16) is turned "OFF" and the position of valves 301 and 321 is changed from "OPEN" to "CLOSE" (Step 436). In the next step of software program, drain pump (11) is turned "OFF" and the valve 305 is changed from position "OPEN" to "CLOSE" (Step 438).

Now, the ultraviolet light, 211, is tuned "ON" (Step 440) for the inputted time value; T4. Once the software program detects that the run time of 211 is equal to the input time value (Step 442), ultraviolet light is turned "OFF" (Step 444).

Again, referring to FIG. 4.0, in the next step the position of valves 303 and 334 is changed from "CLOSE" to "OPEN" (Step 446) and medicine pump 12 is turned "ON" (Step 448) to deliver medicine 501. Software program checks if the delivered volume of medicine is equal to the input value, M1 (Step 450) and once the volume condition is met, position of valve 303 is changed from "OPEN" to "CLOSE" and pump 12 is turned "OFF" (Step 452). While the valve 334 is still in "OPEN" position, the valve 304 is changed from position "CLOSE" to "OPEN" (Step 454) and pump 13 is turned "ON" (Step 456) to deliver medicine 502 to the wound. Once the delivered volume of medicine 502 to the wound is equal to inputted variable value, M2 (Step 458), position of valves 304 and 334 are changed from "OPEN" to "CLOSE" and pump 13 is turned "OFF" (Step 460).

Next, the position of valves 302 and 321 is changed from "CLOSE" to "OPEN" (Step 462) and pump 14 is turned "ON" (Step 464) to deliver the medicine 503 to the wound. Once the delivered volume of medicine 503 to the wound is equal to inputted variable value, M3, (Step 466) the position of valve 302 is changed from "OPEN" to "CLOSE" and pump 14 is turned "OFF" (Step 468). While the valve 321 is still in "OPEN" position, the valve 306 is changed from position "CLOSE" to "OPEN" (Step 470) and pump 15 is turned "ON" (Step 472) to deliver the medicine 504 to the wound. Once the delivered volume of medicine 504 to the wound is equal to inputted variable M4 (Step 474), the position of valves 321 and 306 are changed from "OPEN" to "CLOSE" and pump 15 is turned "OFF" (Step 476). At the next step, the automated program cycle is concluded.

During the execution of the program if the system detects any abnormalities, it creates a beep and displays a message for the user to take appropriate action.

The invention claimed is:

1. A device for protecting against microbial infection, the device comprising:
   a flexible cover having a concave interior surface and a flange configured for sealing engagement with the skin of a patient for affixing the cover to the skin of said patient;
   a first unidirectional inlet tube embedded in the flexible cover and extending therefrom, the inlet tube in fluid communication with the interior thereof and configured to deliver a fluid compound thereto;
   a second unidirectional inlet tube embedded in said flexible cover in a concentric configuration opposing that of the first inlet tube, the second inlet tube in fluid communication with the interior of said flexible cover;
   wherein when fluid moves through the first inlet tube and the second inlet tube, the fluid in the first inlet tube necessarily moves in opposite concentric motion to the fluid in the second inlet tube.

2. The device according to claim 1, further comprising a sensor embedded in the flexible cover.

3. The device according to claim 1, wherein the flange comprises a trough extending along a perimeter thereof, the flexible cover further comprising a trough opening defined in a wall of said trough and in fluid communication with the interior thereof for creation of a negative pressure within the trough.

4. The device according to claim 1, further comprising an ultrasonic transducer embedded in the flexible cover.

5. The device according to claim 1, further comprising a port defined by said flexible cover and configured to receive a camera there, and a camera affixed to said port and positioned to provide an interior view of said flexible cover.

6. A system for treating a wound of a patient in need thereof, the system comprising: a flexible cover having a concave interior surface and a flange configured for sealing engagement with the skin of a patient for affixing the cover to the skin of said patient; an inlet tube embedded in the flexible cover and extending therefrom, the inlet tube in fluid communication with the interior thereof and configured to deliver a fluid compound thereto; and an outlet tube extending from the flexible cover and in fluid communication with the interior thereof configured to allow aspiration of a fluid from the interior thereof;
   a manifold in fluid communication with said inlet tube; an ultrasonic transducer embedded in the flexible cover;
   an ultra-violet light source embedded in the flexible cover;
   a saline reservoir in fluid communication with said manifold inlet tube;
   an oxygen reservoir in fluid communication with said manifold inlet tube;
   a medicament reservoir in fluid communication with said manifold inlet tube;
   and a programmable control system in electronic communication with said ultrasonic transducer, said ultra-violet light source, said manifold, at least one inlet pump configured to deliver a saline solution, a quantity of oxygen, and a medicament to the interior of said flexible cover via said inlet tube, and an outlet pump configured to drain a fluid from the interior of said flexible cover via said outlet tube, wherein the programmable control system is programmed by a user of the system to alternately provide ultrasonic vibration, ultra-violet light, saline, oxygen, and a medicament to the wound area within the flexible cover according to a schedule determined by said user, and further wherein said manifold is adapted to allow alternate flow of said saline, said oxygen, and said medicament to said inlet tube.

7. The system according to claim 6, wherein the programmable control system comprises a cleaning cycle, a medication cycle, and a controlled-environment cycle.

8. The system according to claim 7, wherein during the cleaning cycle the system alternately provides saline and oxygen through said inlet tube.

9. The system according to claim 7, wherein during the medication cycle the system provides medication through said inlet tube.

10. The system according to claim 7, wherein during the controlled environment cycle the system provides oxygen through said inlet tube.

11. The system according to claim 7, wherein between each of said cleaning, medication, and controlled environment cycles, and before another of said cycles, the system drains the contents of the previous cycle via said outlet tube.

* * * * *